US006761905B2

(12) United States Patent
Yeh et al.

(10) Patent No.: US 6,761,905 B2
(45) Date of Patent: Jul. 13, 2004

(54) PROCESS FOR THE PREPARATION OF DIRECT TABLETTING FORMULATIONS AND AIDS

(75) Inventors: Ta-Shuong Yeh, Taipei (TW); Daniel Hungting Yeh, Taipei (TW)

(73) Assignee: Wei Ming Pharmaceutical Mfg. Co., Ltd., Taipei (TW)

( * ) Notice: Subject to any disclaimer, the term of this patent is extended or adjusted under 35 U.S.C. 154(b) by 0 days.

(21) Appl. No.: 09/847,017

(22) Filed: May 1, 2001

(65) Prior Publication Data

US 2003/0017198 A1 Jan. 23, 2003

(51) Int. Cl.⁷ .............................. A61K 9/16; A61K 9/20; A61K 9/48
(52) U.S. Cl. ...................... 424/464; 424/465; 424/451; 424/489; 514/770; 514/772.3; 514/777; 514/778; 514/781; 514/951; 514/960; 514/961
(58) Field of Search ................................ 424/464, 489, 424/499, 458, 465

(56) References Cited

U.S. PATENT DOCUMENTS

| | | | |
|---|---|---|---|
| 4,072,535 A | 2/1978 | Short et al. .................. 106/210 |
| 4,757,090 A | 7/1988 | Salpekar et al. ............. 514/613 |
| 4,800,086 A | 1/1989 | Buehler et al. .............. 424/497 |
| 4,968,509 A | 11/1990 | Radebaugh et al. | |
| 5,006,345 A | 4/1991 | Lang | |
| 5,200,193 A | 4/1993 | Radebaugh et al. | |
| 5,667,807 A | 9/1997 | Hürner et al. .............. 424/489 |
| 5,840,769 A | 11/1998 | Kolter et al. | |
| 6,083,430 A | 7/2000 | Fuisz et al. .................... 264/5 |
| 6,103,219 A | 8/2000 | Sherwood et al. | |
| 6,350,751 B1 * | 2/2002 | Hughes et al. ......... 514/252.16 |

FOREIGN PATENT DOCUMENTS

| | | |
|---|---|---|
| DE | 3506276 C1 | 4/1986 |
| DE | 3505433 A1 | 8/1986 |
| EP | 0273209 | 11/1987 |
| EP | 0 487 774 * | 6/1992 |
| WO | WO 93/09763 | 5/1993 |
| WO | WO 00/06125 | 2/2000 |

OTHER PUBLICATIONS

Rugnic Oral Solid Dosage Forms Remington: the Science and Practice of Pharmacy CH 92:1619 and 6124–1625 1995.*
Ansel et al Pharmaceutical Dosage Forms and Drug Delivery Systems Ch7: 185–186 1999.*
USP24/NF 19, Povidone Monograph.
Shekunov et al., J. of Crystal Growth, 211(1–4):122–130 (2000).

* cited by examiner

Primary Examiner—James M. Spear
(74) Attorney, Agent, or Firm—Morrison & Foerster LLP

(57) ABSTRACT

A thermal adhesion granulation process for preparing direct tabletting formulations or aids is disclosed. The process comprises the step of subjecting all or part of a mixture comprising:
  A) from about 5 to about 99% by weight of one or more diluent excipients and/or from 0 to about 99% by weight of a pharmaceutically active ingredient;
  B) from about 1 to about 95% by weight of a binder excipient; optionally with,
  C) from 0 to about 10% by weight of a disintegrant excipient;
to heating at a temperature in the range of from about 30 to about 130° C. under the condition of low moisture or low content of a pharmaceutically-acceptable organic solvent in a closed system under mixing by tumble rotation until the formation of granules.

54 Claims, No Drawings

PROCESS FOR THE PREPARATION OF DIRECT TABLETTING FORMULATIONS AND AIDS

BACKGROUND OF THE INVENTION

1. Field of the Invention

The present invention relates to a novel granulation process for the preparation of direct tabletting formulations for pharmaceutically-active ingredients, or direct pharmaceutical tabletting aids using pharmaceutical excipients. In particular, this novel granulation process is performed under the condition of low moisture content or low content of a pharmaceutically-acceptable solvent by subjecting a mixture containing one or more diluents and/or active ingredients; a binder; and optionally a disintegrant, to heating in a dosed system under mixing by tumble rotation.

The invention furthermore relates to tablets, capsules, or pellets, which comprise such direct tabletting formulations or tabletting aids, and to processes for producing the tablets, capsules, or pellets comprising the direct tabletting formulations or tabletting aids according to the present invention.

2. Description of the Related Art

The modern tabletting process often involves the compression of direct tabletting aids (excipients), along with active substances, into a tablet under pressure. Direct tabletting aids are required to have not only good flow properties and binding capacity but also a high uptake capacity for active substances, which are generally difficult to compress. This is also true for developing a directly compressible formulation for any pharmaceutically active ingredients. Optimally, the resulting tablets are generally intended to have low friability and high fracture resistance. Some of these requirements are contradictory. For example, high tablet fracture resistance is associated with the presence of many points of contact between the diluent (filler) or pharmaceutically active ingredient and binder inside the tablet, which is usually achieved with the use of diluent and binder in the form of fine particles. However, fine-particle substances in turn have poor flow properties, limiting their suitability for use in high-speed processes. Attempts have been made over the years to improve or modify the diluents (or pharmaceutically active ingredient) and binders so that these contradictory properties are substantially eliminated while retaining the beneficial characteristics.

Direct tabletting aids of this type, which are also referred to as "multipurpose excipients", are, as a rule, preparations which are produced via specific processes, consist of a plurality of components and are also mentioned as co-processed materials in the literature. For example, a combination of α-lactose monohydrate and powdered cellulose is disclosed for direct tabletting in DE-C 3 506 276. Although this composition has a high binding capacity, it has no disintegration-promoting properties, especially when the compressive forces are relatively high. Another combination of α-lactose monohydrate and polyvinyl pyrrolidone as binder, and crosslinked, insoluble polyvinyl pyrrolidone to promote disintegration, disclosed in DE-A 35 05 433 (U.S. Pat. No. 5,006,345), has excellent flow properties and results, without further addition of a disintegrant, in rapidly disintegrating tablets. However, this direct tabletting aid is less suitable for high-dose active substances whose compressibility is poor, because its uptake capacity for active substances to form tablets with sufficient mechanical stability is limited.

U.S. Pat. No. 5,840,769 described a direct tabletting aid using microcrystalline cellulose (MCC) as diluent, soluble polyvinyl pyrrolidone (PVP) as binder, and crospovidone as disintegrant. It was taught that this product can be prepared by conventional wet granulation methods such as mixer granulation, Shugi granulation, extrusion, perforated plate granulation, or preferably, fluidized bed granulation. Wet Granulation of excipients (diluents or disintegrants) or pharmaceutically active ingredients, using a binder, such as PVP, dissolved in water and/or organic solvents, is a common practice. However despite its widespread usage, wet granulation is a process with certain fundamental drawbacks.

The technique of wet granulation is often employed in the pharmaceutical industry to improve the properties of a tabletting mixture. Wet granulation involves the addition of a binder solution to aggregate smaller particles into larger granules for the improvement of powder flowability. Due to the even distribution of the binder on the surface of the diluent or active ingredient, thereby increasing the points of contact, binding efficiency of the resulting granules is often increased and results in greater tablet strength. Granulation also serves to reduce dust in the tabletting mixture and improve workplace conditions during the automated tabletting processes. Another benefit of wet granulation is that it helps to facilitate the uniform blending of components in a tabletting mixture.

Wet granulation requires a large amount of liquid to be added, which necessitates tanks and handling equipments. Since the liquid used in wet granulation must subsequently be removed, a drying step is also needed, thereby requiring drying equipment and further complicating the manufacturing process, as well as significantly increasing the energy, cost and production time of the overall process. Furthermore, the use of large amounts of volatile organic solvent as granulating fluid may be harmful to the operator as well as the environment Special precaution and equipments are necessary to avoid explosions and protect workers from exposure to these solvents.

Another disadvantage of wet granulation is that, in certain instances, the presence of excessive moisture can negatively affect the ingredients in the tabletting formulation. For example, as discussed in U.S. Pat. No. 6,103,219, it is known that the exposure of microcrystalline cellulose to moisture in the wet granulation process severely reduces the compressibility of this excipient, mainly due to softening of the cellulose fibers. This loss of tabletting strength dictates that a larger amount of the MCC may be needed to obtain an acceptably compressed final product, especially when a high dose of active ingredients is sought The additional amount of MCC required not only adds cost to the preparation, but more importantly, increases the size and bulk of the resulting tablet, making it more difficult to swallow. The loss of compressibility of microcrystalline cellulose caused by wet granulation has long been considered a problem in the art for which there has been no satisfactory solution.

The literature is flooded with various examples for the use of PVP (or other binders) in wet granulation (eg., WO 93/09763; WO 00/06125; U.S. Pat. No. 4,968,509; U.S. Pat. No. 5,200,193; U.S. Pat. No. 5,462,747). By in large, wet granulation with a large amount of aqueous or alcoholic solution to dissolve the binder is still the most popular way to prepare granules for tabletting or to manufacture matrix-forming material for sustained-release dosage forms Considering the drawbacks of wet granulation, it would be desirable to obtain an alternative granulation process which improves the flowability, while retaining or improving other tabletting features, such as tablet hardness, of a direct tabletting formulation or aid, without the extensive use of granulation liquid as employed in wet granulation.

SUMMARY OF THE INVENTION

Thus, the object of the present invention is to develop an alternative granulation process which utilizes considerably less water or solvent than the traditional wet granulation method.

Another object of the present invention is to utilize the granulation process for providing direct tabletting formulations with good flow properties and binding capacity to form tablets of low friability and adequate hardness.

A further object of the present invention is to utilize the granulation process for producing direct tabletting aids which, while having good flow properties and binding capacity to form tablets of low friability and adequate hardness, have a high uptake capacity for active substances whose tablettability is poor.

An additional object of the present invention is to utilize the granulation process for providing direct tabletting formulations or aids which, while having good flow properties and binding capacity to form tablets of low friability and adequate hardness, have an adequate disintegration activity for active substances.

Further objects and advantages of this invention will become apparent from a consideration of the ensuing discussions and examples.

As a result of various investigations carried out to find a novel method achieving the purpose, the present inventors found that when a finely-divided powder of binder is mixed with diluent excipients such as cellulose powder, microcrystalline cellulose, lactose, starch, dibasic calcium phosphate, or active substances, such as acetaminophen or ascorbic acid, and subjected to heating in a closed system with a low moisture content or low content of a pharmaceutically-acceptable solvent, while mixed by rumble rotation, it was possible to obtain direct tabletting formulations or aids with favorable properties not observed in the starting materials.

Thus, the present invention provides a novel method to prepare a direct tabletting formulations or aids using a finely-divided powder of binder to granulate excipients or active substances in a closed system with a low moisture content or low content of a pharmaceutically-acceptable solvent while being subjected to heating and mixing by tumble rotation.

DETAILED DESCRIPTION OF THE INVENTION

The present invention, termed "thermal adhesion granulation" (TAG), is a novel granulation method and will be described in detail below.

The present invention provides a granulation process for preparing direct tabletting formulations containing pharmaceutically-active ingredients, or direct tabletting aids (i.e., aids which contain no active substances), by subjecting the mixture of A) and B) in the following to heating at a temperature range of from about 30 to about 130° C., preferably from about 40 to about 110° C., and in particular from about 60 to about 105° C., under the condition of from about 0.1 to about 20% initial moisture content and/or from about 0.1 to about 20% initial content of a pharmaceutically-acceptable organic solvent, in a dosed system under mixing by tumble rotation until the formation of granules:

A) from about 5 to about 99% by weight, preferably from about 10 to about 90% by weight, of one or more diluent (filler) excipients suitable for tabletting, and/or from 0 to about 99% by weight, preferably from about 10 to about 90% by weight, of a pharmaceutically-active ingredient;

B) from about 1 to about 95% by weight, preferably from about 5 to about 50% by weight, of a binder excipient; and optionally, C) from 0 to about 10% by weight of disintegrant excipient, which can be added to the above mixture of A) and B) before or after granulation.

The granulation of a mixture of components A), B) and optionally C), according to the present invention, must be conducted in a closed system with initial moisture content of the mixtures in the range of from about 0.1 to about 20%, preferably in a range of from about 2 to about 15%, and more preferably from about 4 to about 10%, as determined by a moisture balance (eg, Ohaus, Japan). Alternatively, granulation may be accomplished with a pharmaceutically-acceptable organic solvent (e.g., ethanol) at an initial solvent content of the mixtures in the range of from about 0.1 to about 20%, preferably in a range of from about 0.1 to about 10%, and more preferably from about 0.5 to about 5%.

"Tumble rotation" is defined as rotation of a container about an inner horizontal axis, whereby the powder mixture mass inside the container is made to slide, roll, flow, fall or otherwise move along the inner wall of the container.

The diluent excipient(s) in component A) may be selected from powdered cellulose, microcrystalline cellulose, lactose, starch, dibasic calcium phosphate, tribasic calcium phosphate, mannitol, sorbitol, sucrose, dextrose, cellulose acetate, hydroxypropyl methylcellulose, and others, or a combination thereof, preferably powdered cellulose, microcrystalline cellulose, lactose, starch, and dibasic calcium phosphate. In a preferred embodiment of the present invention, the microcrystalline used is grade 101, wherein about 90% of the particles are in the range from about 1 $\mu$m to about 125 $\mu$m, and the average particle size is from about 10 $\mu$m to about 70 $\mu$m.

The pharmaceutically-active ingredient in component A) may be selected from acetaminophen, ascorbic acid, nifedipine, ibuprofen, aspirin, and others, or a combination thereof, preferably acetaminophen and ascorbic acid.

Although stable tablets can usually be obtained with diluent excipient such as powdered cellulose, microcrystalline cellulose, lactose, starch, and dibasic calcium phosphate, even with low compressive forces, the flow properties of these fine powders are generally poor due to the relatively small particle sizes. Granulation with binders improves the flow properties due to the increase in particle size talking place during granulation.

For component B), the binder excipient may be selected from soluble polyvinyl pyrrolidone (PVP), hydroxypropylcellulose (HPC), hydroxypropyl methylcellulose (HPMC), low-substituted hydroxypropylcellulose (L-HPC), sodium carboxymethylcellulose, methyl cellulose, ethyl cellulose, sugar, and others, or a combination thereof, preferably polyvinyl pyrrolidone and hydroxypropylcellulose. Further, the binder excipient may contain from 0 to about 10% (by weight with respect to the binder) of one or more anticaking agents, such as dibasic calcium phosphate anhydrous, silicon dioxide, or calcium silicate, preferably dibasic calcium phosphate anhydrous.

For component C), disintegrating agents such as crospovidone (PVP-CL), sodium starch glycolate (SSG), reticulated (crosslinked) carboxymethylcellulose (CMC-CL), low-substituted hydroxypropylcellulose (L-HPC), and others, or a combination thereon may be mixed with the mixture during granulation (intragranular) or after granulation (extragranular) to further facilitate the disintegration of the resulting tablets or capsules.

Soluble polyvinyl pyrrolidone (PVP), used in the present invention as a preferred binder in one embodiment of the thermal adhesion granulation process, is a finely-divided powder applied extensively in the pharmaceutical industry as a tabletting binder, either for wet granulation or direct compression. Generally, the polyvinyl pyrrolidones have a K value of from about 12 to about 120. Particularly preferred polyvinyl pyrrolidones according to the invention have a K value of from about 20 to about 95, in particular from about 25 to about 35. For the definition of the K value, reference may be made to the povidone monograph in U.S. Pat. No. 24/NF19 (2000).

Thermal adhesion granulation is essentially a dry process in which the binder is dry-blended into the mixture, rather than added as a solution. To optimize the binding efficiency, it is desirable to use a finely-divided binder powder to maximize the contact points between the binder and the diluent or active ingredients. Certain binders, such as PVP, are highly hygroscopic and become sticky and tacky with the absorption of moisture. Caking of fine-particle PVP during storage, as a result of absorbing moisture from the atmosphere, is a common occurrence. To help promote and maintain the uniform distribution of the binder as a fine powder (component B) when mixed with the diluents and/or active ingredients (component A), the binder used in this invention can be first mixed with from 0 to about 10%, preferably from about 0.01 to about 10%, more preferably from about 2 to about 4% (by weight with respect to binder), of an anticaking agent. In applying the anticaking agent, the binder and the anticaking agent should be blended together, pulverized to a fine powder in a blender, then passed through a 200-mesh sieve. This binder/anticaking agent mixture can then be used for granulation with component A and optionally component C.

The low water or solvent requirement for TAG stems from the fact that the granulation is conducted in a closed system. Because vapors generated from heating (from the added wetting solution plus any inherent moisture of the powder mass) are prevented from escaping from the system, granulation fluid usage is maximized and the granulation can be accomplished with a minimal addition of moisture or solvent. It is believed that the heating of the powder mass may also result in the transfer of certain inherent moisture in the diluents to the binder. A preferred embodiment of TAG is that the heat distribution on the surface of the granulation vessel should be, in some manner, slightly non-uniform, such that when the powder mass is heated, the evolved water or solvent vapor can condense on a portion of the inner surface of the vessel which is comparatively cooler. Since binders, e.g., PVP, are generally highly hygroscopic, any moisture present in the system, especially in the form of condensation, is scavenged by the binder, which then becomes sticky and tacky with the absorption of moisture and heat. Because the binder was uniformly predispersed among the diluents/active ingredients as a fine powder prior to granulation, the increasing adhesiveness of the binder results in the cohesion of neighboring particles and ultimately the formation of granules as the powder mass is mixed within the dosed vessel. The optimal temperature range for TAG is system-specific, and depends on factors such as the type and amount of diluents, binder and granulation fluid used. For example, when an organic solvent rather than water is used as the granulation fluid, a lower temperature may be necessary.

Compared with the known techniques of mixing and tabletting active substances with powdered cellulose, microcrystalline cellulose, crosslinked polyvinyl pyrrolidone and water-soluble polyvinyl pyrrolidone, as described in, for example, EP-A 273 209 or U.S. Pat. No. 5,840,769, a tabletting process using the direct tabletting aid according to the invention is distinguished by being a significantly simplified production process with relatively low energy requirement, minimal pollution potential and a wide range of applicability with regard to the excipients, binders and active substance employed. These advantages can be attributed mainly to the low amount or water or organic solvent required by the present invention as granulation fluids to produce granules which are comparable or superior in performance compared to granules derived from existing technologies.

The present invention, "thermal adhesion granulation," differs from the traditional wet granulation approach in several important aspects:

1) In thermal adhesion granulation, a low amount of moisture is added to the tabletting mixture already containing diluent excipients and binder, whereas in wet granulation the binder is generally dissolved in the granulation fluid then mixed with the diluent excipients.

2) Thermal adhesion granulation resembles a "dry" process in that the granulation fluid requirement (water or organic solvent) of thermal adhesion granulation is significantly less than that in wet granulation.

3) With the exception of the drying step, wet granulation is typically conducted at the ambient temperature, whereas in thermal adhesion granulation the tabletting mixture is heated to promote the formation of granules.

4) In wet granulation, the mixing requirement is typically accomplished by either directly stirring the powder/fluid mixture or mass with a blade, arm, propeller, chopper, or other types of mechanical stirring means (e.g., shear granulation using a planetary mixer, high speed mixer/granulator), or suspending the powder in a hot stream of air while spraying with a binder solution (fluidized bed granulators). In the former, granules are formed by sieving the wet mass, while in the latter, granules are formed by coating the particles with the binder solution. In thermal adhesion granulation, granules are formed during mixing of the moist powder under continuous tumble rotation, as the heated powder mass flows within the container and agglomerates with the aid of the binder.

5) Wet granulation involves significant post-granulation steps of drying and milling to form the desired granules. These steps are unnecessary in the present invention due to the low amount of moisture introduced to the tabletting mixture.

6) Conventional granulation methods are typically conducted in open systems. The present invention of thermal adhesion granulation is conducted in a closed system.

An advantage of being able to conduct granulation in a dosed system is that system conditions may be manipulated to a high degree of specificity, depending on the reactor configuration. For example, in a mixer capable of heating and vacuum drying, the headspace gas may either be withdrawn to a complete or partial vacuum, or purged and replaced with inert or nonreactive gases (e.g., nitrogen or helium). Although heat is applied, granulation in a system devoid of oxygen can lead to greater drug stability as well as decreased likelihood of solvent explosion. In the same reactor, a post-granulation vacuum drying step could also be applied for efficient solvent recovery.

Another major advantage of granulating pharmaceutical products in a closed system is that it helps to minimize the generation of dust during powder processing. This technique serves to contain fine-powder active ingredients whose spread or loss from the system is not desirable due to their cost or biological activity. Just as applicable, the TAG process may be utilized in other industries such as nutraceutical, food, or animal feed, among others.

The application of TAG may be further extended to the granulation of other industrial or agricultural products—such as fertilizer or pesticide powders, granules or pellets—for which granulation it a closed system may help to reduce the generation of toxic or hazardous dust.

Thee present invention is also related to a powder mixture of soluble polyvinyl pyrrolidone containing from about 0.01 to about 10% (by weight with respect to the polyvinyl pyrrolidone) of dibasic calcium phosphate anhydrous.

The present invention is further related to a direct tabletting formulation or aid comprising:

i) from about 5 to about 99% by weight of powder cellulose, microcrystalline cellulose, lactose, starch, or dibasic calcium phosphate;

ii) from 0 to about 99% by weight of acetaminophen or ascorbic acid;

iii) from about 1 to about 95% by weight of a soluble polyvinyl pyrrolidone which contains from about 0.01 to about 10% (by weight with respect to the polyvinyl pyrrolidone) of dibasic calcium phosphate anhydrous; and iv) from 0 to about 10% by weight of crospovidone, sodium starch glycolate, reticulated carboxymethylcellulose, or low-substituted hydroxypropylcellulose.

The present invention furthermore relates to tablets, capsules, or pellets, which comprise the direct tabletting formulations or tabletting aids disclosed in the present invention, and to processes for producing such said tablets, capsules, or pellets.

The present invention is specifically described below in the following examples. These examples are intended to be illustrative only and are not intended to limit the scope of the present invention.

EXAMPLES

The diluent (filler) excipients used in the examples of this invention comprise of microcrystalline cellulose grade 101 (MCC 101), lactose (lactose anhydrous, Borculo), starch (starch 1500, Colorcon), and dibasic calcium phosphate anhydrous (DCP, Fujicalin SG, Fuji Chemical). These diluents were selected because they represent some of the more frequently utilized tabletting diluents. The use of these diluents is to demonstrate the wide range of application of the present invention and should not be interpreted as a limitation of the scope of the present invention. The basic physical and tabletting properties of these diluents, as well as those of Ludipress® (consisting of 93% by weight of lactose, 3.5% by weight of Kollidong® 30 and 3.5% by weight of Kollidon® C.L, BASF) and with Avicel® PH 200, a microcrystine cellulose (FMC Corporation), are listed in Table 1. In all examples of this invention, dibasic calcium phosphate anhydrous (Fujicalin, Fuji Chemical, Japan) was added to the binder in an amount of about 3% (by weight with respect to the binder) as an anticaking agent. Thus, it should be noted that the percentages of binders expressed in the subsequent examples are nominal percentages (i.e., they also include a small amount of dibasic calcium phosphate anhydrous).

To determine the powder characteristics of the excipients, granules and direct tabletting aids described within this invention, the following parameters were measured: mean particle size (through sieve analysis using 37 $\mu$m to 800 $\mu$m size sieves), powder repose angle, powder bulk density, and powder tapped density (A.B.D. Fine Particle Characteristics Measuring Instrument, Tsutsui Japan). The ease of powder flow is represented by both the repose angle and the Carr's index, calculated as follows:

Carr's index (%)=(tapped density−bulk density)/tapped density× 100% where lower values of the repose angle and the Carr's index represent better powder flow. To characterize tablets made using the excipients, granules and direct tabletting aids described within this invention, tablets (11.3 mm discoid, 0.5 g) were produced under a compression pressure of 49 MPa (500 Kg) using the Sankyo Pio-Tech SK-02 Tablettability Tester japan). Tablet hardness (tensile strength measured diametrically) was tested on the same instrument. Tablet friability and disintegration time were tested on an Aikho japan) AE-20 Roche Friabilator (20 rpm; 5 min; n=10) and a Shin Gwon (Taiwan) SK-0004 tablet disintegration tester (n=6), respectively.

TABLE 1

| Properties | MCC 101 | Lactose | Starch | DCP | Ludi-press ® | Avicel ® PH 200 |
|---|---|---|---|---|---|---|
| Mean Size ($\mu$m) | 50 | 90 | 80 | 113 | 170 | 180 |
| Angle of Repose (deg.)[a] | 54.33 ± 1.53 | 40.33 ± 0.58 | 40.68 ± 0.58 | 41.33 ± 0.58 | 35.67 ± 0.58 | 46.00 ± 1.00 |
| Bulk Density (g/ml)[a] | 0.256 ± 0.002 | 0.635 ± 0.006 | 0.623 ± 0.007 | 0.387 ± 0.002 | 0.527 ± 0.002 | 0.324 ± 0.001 |
| Tapped Density (g/ml)[a] | 0.397 ± 0.002 | 0.811 ± 0.011 | 0.784 ± 0.006 | 0.455 ± 0.002 | 0.600 ± 0.002 | 0.411 ± 0.001 |
| Carr's Index (%)[a] | 35.58 ± 0.71 | 21.63 ± 0.34 | 20.56 ± 0.21 | 14.94 ± 0.14 | 12.20 ± 0.53 | 21.04 ± 0.35 |
| Tensile Strength (MPa)[b] | 2.677 ± 0.493 | NT[c] | 0.191 ± 0.017 | NT[c] | 0.302 ± 0.043 | 3.154 ± 0.373 |
| Friability (%) | 0.20 | NT[c] | 1.03 | NT[c] | 2.99 | 0.20 |
| Disintegration (sec) | >900 | NT[c] | <420 | NT[c] | <40 | <440 |

[a]mean ± SD, n = 3;
[b]mean ± SD, n = 10;
[c]NT: not tablettable at 500 kg (49 MPa) under testing conditions.

Example 1

Production of the Direct Tabletting Aids with Different Diluent Excipients

The direct tabletting aids were produced by the method disclosed, which outlines the general technique of the thermal adhesion granulation process. For this, water-soluble polyvinyl pyrrolidone (Kollidon® 30, BASF) with a K value of about 30 (hereafter referred to as PVP K30), containing within it about 3% dibasic calcium phosphate anhydrous, was mixed either with microcrystalline cellulose grade 101 (Granule A), lactose (Granule B), starch (Granule C), or dibasic calcium phosphate (Granule D) at a PVP ratio of 10% by weight with respect to the total mixture. The binder/diluent mixture was next moisturized with an additional 5% water (by weight of the total mixture) via a fine spray and blended briefly. The mixture was next placed in a prewarmed glass bottle, sealed close, and then subjected to heating by infrared lamp at 90–105° C. while mixed under tumble rotation (the bottle is subjected to a rolling motion about a horizontal axis) for 3 to 20 min. until the formation of granules. During the granulation, the bottle was also briefly shaken periodically for the powder mass to contact any accumulated vapor condensation on the inner surface of the bottle. The resulting granules were then screened immediately through a size 24 mesh (800 μm). The resulting granules may be used directly upon cooling, or, in certain cases if so desired, may be dried further by the infrared lamp or by other means as necessary. This granulation process produced granule compositions with the properties listed in Table 2A. It can be seen that, referring to Table 1, Granules A–D exhibited significant improvements in particle size, density, flowability, tablet strength, and disintegration time when compared with their respective parent materials (diluents). In addition to the diluents used in Granules A–D, the TAG process could also be applied to the granulation of other diluents, or different grades of MCC, lactose, starch, or DCP. For example, yet larger granules could be obtained with the use of a microcrystalline cellulose of a larger size grade as the parent material (e.g., grade 102 with a mean particle size of 90 μm).

Example 3

Production of the Direct Tabletting Aids with PVP at a Larger Percentage

The direct tabletting aids were produced in accordance with the general method disclosed in Example 1. For this example, PVP K30 at a percentage of 50% was mixed either with microcrystalline cellulose grade 101 (Granule H), lactose (Granule I), starch (Granule J), or dibasic calcium phosphate (Granule K) and then was subjected to the thermal adhesion granulation process. The moisture added to the mixtures was about 5%. This process resulted in the granule compositions compiled in Table 2B. It can be seen that the use of PVP K30 at a percentage of 50% led to a decrease in particle size as compared to Granules A, B, C and D which were made at a PVP K30 content of 10%.

TABLE 2A

|  | Granule A | Granule B | Granule C | Granule D | Granule E | Granule F | Granule G |
|---|---|---|---|---|---|---|---|
| % Composition |  |  |  |  |  |  |  |
| MCC 101 | 90.0 |  |  |  | 95.0 | 90.0 | 85.0 |
| Lactose |  | 90.0 |  |  |  |  |  |
| Starch |  |  | 90.0 |  |  |  |  |
| DCP |  |  |  | 90.0 |  |  |  |
| PVP K30 | 10.0 | 10.0 | 10.0 | 10.0 | 5.0 | 10.0 | 15.0 |
| Mean Size (μm) | 212.4 | 326.0 | 515.2 | 200.7 | 123.0 | 239.9 | 419.0 |
| Angle of Repose (deg.)[a] | 42.67 ± 0.58 | 35.00 ± 1.00 | 38.33 ± 0.58 | 32.00 ± 0.00 | 49.33 ± 1.53 | 43.00 ± 1.00 | 41.33 ± 1.00 |
| Bulk Density (g/ml)[a] | 0.205 ± 0.003 | 0.524 ± 0.004 | 0.443 ± 0.003 | 0.454 ± 0.002 | 0.216 ± 0.001 | 0.213 ± 0.002 | 0.223 ± 0.004 |
| Tapped Density (g/ml)[a] | 0.255 ± 0.001 | 0.561 ± 0.005 | 0.458 ± 0.001 | 0.505 ± 0.003 | 0.291 ± 0.001 | 0.253 ± 0.002 | 0.245 ± 0.004 |
| Carr's Index (%)[a] | 19.69 ± 0.88 | 6.52 ± 0.08 | 3.17 ± 0.69 | 10.08 ± 0.86 | 25.58 ± 0.23 | 15.59 ± 0.29 | 9.11 ± 0.74 |
| Tensile Strength (MPa)[b] | 3.077 ± 0.329 | 2.234 ± 0.802 | 1.077 ± 0.161 | 1.162 ± 0.124 | 3.324 ± 0.469 | 3.125 ± 0.205 | 3.529 ± 0.264 |
| Friability (%) | 0 | 0.60 | 0.81 | 1.42 | 0.20 | 0.40 | 0 |
| Disintegration (sec) | >900 | <375 | <190 | <180 | >900 | >900 | >900 |

[a]mean ± SD, n = 3;
[b]mean ± SD, n = 10

Example 2

Production of the Direct Tabletting Aids with PVP at Different Percentages

The direct tabletting aids were produced in accordance with the general method disclosed in Example 1. For this example, PVP K30 at different percentages [5% (Granule E), 10% (Granule F), and 15% (Granule G)] was mixed with microcrystalline cellulose grade 101 and then was subjected to the thermal adhesion granulation process. The moisture added to the mixtures was about 5%. This process resulted in the granule compositions compiled in Table 2A. It can be seen that granule size, and accordingly flowability, increased with additional amount of PVP used for the mixture. Differences in the tabletting tensile strengths of the three granules were not statistically significant.

Example 4

Production of the Direct Tabletting Aids with PVP at Different Moisture Content

The direct tabletting aids were produced in accordance with the general method disclosed in Example 1. For this example, PVP K30 at a fixed ratio (100/%) was mixed with microcrystalline cellulose at different levels of moisture added to the mixture [about 5% (Granule L), about 10% (Granule M), about 15% (Granule N)] and then was subjected to the thermal adhesion granulation process. This process resulted in the granule compositions compiled in Table 2B. It can be seen that, of the three moisture levels tested, 5% moisture addition produced the largest particle size and best flowability. It can also be seen that increased water content actually led to decreased granule formation and that the present invention, in a significant departure from conventional wet granulation processes, was implemented optimally under low moisture content. Furthermore, the close similarity of the properties of Granule A, F, and L, which were compositionally identical, served to verify the repeatability of the thermal adhesion granulation process.

TABLE 2B

| | Granule H | Granule I | Granule J | Granule K | Granule L | Granule M | Granule N |
|---|---|---|---|---|---|---|---|
| % Composition | | | | | | | |
| MCC 101 | 50.0 | | | | 90.0 | 90.0 | 90.0 |
| Lactose | | 50.0 | | | | | |
| Starch | | | 50.0 | | | | |
| DCP | | | | 50.0 | | | |
| PVP K30 | 50.0 | 50.0 | 50.0 | 50.0 | 10.0 | 10.0 | 10.0 |
| (Moisture added) | | | | | (5%) | (10%) | (15%) |
| Mean Size (μm) | 162.6 | 204.7 | 151.4 | 195.1 | 196.1 | 156.6 | 144.8 |
| Angle of Repose (deg.)[a] | 49.00 ± 1.00 | 44.33 ± 3.51 | 38.67 ± 1.16 | 38.33 ± 0.58 | 44.67 ± 0.58 | 50.00 ± 1.00 | 56.33 ± 0.58 |
| Bulk Density (g/ml)[a] | 0.296 ± 0.002 | 0.430 ± 0.001 | 0.425 ± 0.001 | 0.415 ± 0.001 | 0.209 ± 0.002 | 0.234 ± 0.001 | 0.239 ± 0.002 |
| Tapped Density (g/ml)[a] | 0.385 ± 0.001 | 0.523 ± 0.001 | 0.531 ± 0.001 | 0.495 ± 0.001 | 0.258 ± 0.001 | 0.301 ± 0.001 | 0.294 ± 0.001 |
| Carr's Index (%)[a] | 23.08 ± 0.56 | 17.82 ± 0.07 | 19.97 ± 0.21 | 16.12 ± 0.17 | 19.17 ± 0.58 | 22.31 ± 0.17 | 18.61 ± 0.23 |
| Tensile Strength (MPa)[b] | 6.931 ± 0.941 | 6.470 ± 1.087 | 4.362 ± 0.907 | 1.284 ± 0.322 | 3.277 ± 0.398 | 2.761 ± 0.212 | 3.197 ± 0.292 |
| Friability (%) | 0 | 0.20 | 0.20 | 0.40 | 0.20 | 0 | 0 |
| Disintegration (sec) | >900 | >900 | >900 | >900 | >900 | >900 | >900 |

[a]mean ± SD, n = 3;
[b]mean ± SD, n = 10

Example 5

Production of the Direct Tabletting Aids by Different Methods in Terms of Binder, Wetting Solution and System Condition The production of the direct tabletting aids by different methods in terms of binder, wetting solution, and system condition was demonstrated in this example. The general method of thermal adhesion granulation was followed in this example, with the changes as specified below. Microcrystalline cellulose grade 101, at 90%, was used in all granules. The compositions and properties of the granules, as well as Granule A from Example 1, can be found in Table 3. Granule A' was compositionally similar to Granule A with the exception that it contained 3.5% crospovidone as an intragranular disintegrant, i.e., the crospovidone was blended with the MCC and the PVP K30 prior to thermal adhesion granulation. For Granule Q, PVP K30 at a percentage of 10% was mixed with microcrystalline cellulose. A low amount of ethanol (about 1.5%) was used as the wetting solution rather than water, as used in previous examples. When granulating with ethanol a heating temperature of 70–90° C. was applied. It can be seen that ethanol could be applied as the wetting solution for thermal adhesion granulation, albeit smaller granules were formed when compared with water-wetted granules (Granule A). For Granule R, hydroxypropylcellulose (HPC, Klucel® EXF, Aqualon) at 10% was mixed with microcrystalline cellulose. Ethanol (about 1.5%) was again used as the wetting solution. It can be seen that the use of HPC produced favorable granules, demonstrating the applicability of the thermal adhesion granulation process to produce tabletting mixtures containing other binders.

As a demonstration of the dosed-system requirement for thermal adhesion granulation, two granulation series (Group T, about 5% water added; Group U, about 1.5% ethanol added), both containing 10% PVP K30 and 90% MCC 101, were attempted in open systems with the glass bottle uncapped. Comparing the mean particle sizes of Group T and U to their dosed system counterparts (Granule A and Q, respectively), it can be seen that thermal adhesion granulation according to the present invention could not be achieved in an open system. This result demonstrates that TAG is not simply a variation of wet granulation performed at a lower moisture level. The failure of Group T and U to form granules also serves to differentiate the present invention from moisture-activated dry granulation (MADG) techniques. The strict requirement for thermal adhesion granulation process to be conducted in a closed system highlights the uniqueness and novelty of the present invention, since conventional granulation processes are routinely carried out in an open system.

TABLE 3

| | Closed system | | | | Open system | |
|---|---|---|---|---|---|---|
| % Composition | Granule A | Granule A' | Granule Q | Granule R | Group T | Group U |
| MCC 101 | 90 | 86.85 | 90 | 90 | 90 | 90 |
| PVP K30 | 10 | 9.65 | 10 | | 10 | 10 |
| HPC | | | | 10 | | |
| Disintegrant (crospovidone) | | 3.5 | | | | |
| Method of wetting | 5% water | 5% water | 1.5% ethanol | 1.5% ethanol | 5% water | 1.5% ethanol |
| Mean size (μm) | 2124 | 139.8 | 76.5 | 98.3 | 56.3 | 53.8 |
| Angle of Repose (deg)[a] | 42.67 ± 0.58 | 45.33 ± 0.58 | 47.67 ± 0.58 | 51.00 ± 1.00 | 47.67 ± 0.58 | 49.67 ± 0.58 |
| Bulk Density (g/ml)[a] | 0.205 ± 0.003 | 0.199 ± 0.002 | 0.231 ± 0.001 | 0.216 ± 0.001 | 0.250 ± 0.002 | 0.292 ± 0.003 |
| Tapped Density (g/ml)[a] | 0.255 ± 0.001 | 0.241 ± 0.001 | 0.320 ± 0.002 | 0.287 ± 0.001 | 0.329 ± 0.002 | 0.400 ± 0.004 |
| Carr's Index (%)[a] | 19.69 ± 0.88 | 17.41 ± 0.43 | 27.77 ± 0.18 | 24.70 ± 0.23 | 23.88 ± 0.28 | 27.01 ± 0.26 |
| Tensile Strength (MPa)[b] | 3.077 ± 0.329 | 3.787 ± 0.192 | 2.457 ± 0.168 | 2.535 ± 0.150 | 1.846 ± 0.457 | 2.139 ± 0.388 |
| Friability (%) | 0 | 0.2 | 1.02 | 0 | 0.40 | 0 |
| Disintegration (sec) | >900 | <180 | >900 | >900 | >900 | >900 |

[a]mean ± SD, n = 3;
[b]mean ± SD, n = 10; A': +3.5% intragranule disintegrant

Example 6

Granulation of Active Substance for Direct Compression Tabletting

The direct tabletting formulation with only active ingredient and no diluent present is produced by the method disclosed. For this, PVP K30 was mixed with acetaminophen (fine powder, BASF) either with disintegrant (Granule 0) or without disintegrant (Granule P) and then was subjected to the thermal adhesion granulation process. The moisture added to the mixtures was about 5%. This method resulted in the granule compositions compiled in Table 4. Prior to granulation, acetaminophen existed as a fine powder (<400mesh, 37 μm) which has extremely poor flowability and cannot be tabletted at all at 500 kg (49 MPa). It can be seen that the TAG process produced acetaminophen granules with significantly improved size and flowability, as well as good tablet strength and disintegration properties.

TABLE 4

| % Composition | Granule O | Granule P |
|---|---|---|
| PVP K30 | 9.65 | 10 |
| Disintegrant (crospovidone) | 3.5 | — |
| Acetaminophen | 86.85 | 90 |
| Mean Size (μm) | 177.2 | 165.0 |
| Angle of Repose (deg)$^a$ | 48.00 ± 1.00 | 53.00 ± 1.00 |
| Bulk Density (g/ml)$^a$ | 0.247 ± 0.003 | 0.283 ± 0.002 |
| Tapped Density (g/ml)$^a$ | 0.303 ± 0.002 | 0.319 ± 0.002 |
| Carr's Index (%)$^a$ | 18.36 ± 0.52 | 11.42 ± 0.01 |
| Tensile Strength (MPa)$^b$ | 0.481 ± 0.057 | 0.808 ± 0.094 |
| Friability (%) | 1.05 | 1.38 |
| Disintegration (sec) | <35 | <55 |

$^a$mean ± SD, n = 3;
$^b$mean ± SD, n = 10

Example 7

Use of the Direct Tabletting Aids for Tablet with Active Substance

The tabletting mixtures described in this example were produced by screening an active substance (ascorbic acid, a hydrophilic drug, in Test 1, and acetaminophen, a hydrophobic drug, in Test 2) through a No. 24 screen (800 μm) and loosely mixing it with the direct tabletting aid produced by the thermal adhesion granulation process as described in Example 1. The powder mixture was mixed for 10 minutes before being used for direct tabletting. Tables 5 and 6 show the tabletting results for formulations using the granules according to the invention (Granules A, B, C and D), compared with formulations using Ludipress® (consisting of 93% by weight of lactose, 3.5% by weight of Kollidon® 30 and 3.5% by weight of Kollidon® C.L) and Avicel® PH 200, a microcrystalline cellulose.

For the MCC-based products, it can be seen that ascorbic acid and acetaminophen formulations using Granule A were at least comparable to those using Avicel® PH200 in terms of tablet strength, disintegration time and friability (Tables 5 and 6). However, Granule A exhibited better flowability over Avicel® PH200 (see Tables 1 and 2A). For the lactose-based products, it can be seen that formulations containing Granule B were superior to formulations containing Ludipress® in all regards.

| | |
|---|---|
| Ascorbic acid crystals | 40.0% by wt |
| Direct tabletting aid | 56.5% by wt |
| Disintegrant (crospovidone) | 3.5% by wt |

TABLE 5

| Direct Tabletting Aid | Tensile Strength [MPa] (mean ± SD; n = 10) | Disintegration time [sec] | Friability [%] |
|---|---|---|---|
| Granule A | 1.296 ± 0.112 | <20 | 0 |
| Granule B | 0.532 ± 0.135 | <20 | 1.21 |
| Granule C | 0.369 ± 0.037 | <150 | 1.95 |
| Granule D | 0.240 ± 0.038 | <45 | 5.49 |
| Avicel ® PH 200 (Comp.) | 1.325 ± 0.120 | <20 | 0.41 |
| Ludipress ® (Comp.) | 0.183 ± 0.043 | <40 | 10.85 |

| | |
|---|---|
| Acetaminophen powder | 30.0% by wt |
| Direct tabletting aid | 66.5% by wt |
| Disintegrants (crospovidone) | 3.5% by wt |

TABLE 6

| Direct Tabletting Aid | Tensile Strength [MPa] (mean ± SD; n = 10) | Disintegration time [sec] | Friability [%] |
|---|---|---|---|
| Granule A | 1.287 ± 0.115 | <26 | 0 |
| Granule B | 0.457 ± 0.090 | <37 | 1.62 |
| Granule C | 0.258 ± 0.025 | <205 | 1.03 |
| Granule D | 0.321 ± 0.050 | <45 | 4.45 |
| Avicel ® PH 200 (Comp.) | 0.826 ± 0.058 | <17 | 0.81 |
| Ludipress ® (Comp.) | 0.173 ± 0.045 | <60 | 5.98 |

Example 8

Production of a Direct Tabletting Formulation Containing Active Substance Using Thermal Adhesion Granulation In the preceding example, the active ingredient and the disintegrant were added extragranularly, i.e., they were blended with the direct tabletting aid produced by TAG, then the mixture was directly compressed into a tablet. The TAG process can also be utilized to granulate all components into a direct tabletting formulation, such that the resulting granules can be directly tabletted without further additions or modifications. In this example, a mixture of the following formula, which is compositionally identical to the Granule A series in Table 6, was subjected to thermal adhesion granulation (with about 5% moisture added), then directly compressed into tablets.

| | |
|---|---|
| Acetaminophen powder | 30.0% by wt |
| MCC 101 | 59.85% by wt |
| PVP K30 | 6.65% by wt |
| Disintegrants (crospovidone) | 3.5% by wt |

The resulting tablets had the following properties: Tensile Strength=1.088±0.167 MPa; Disintegration time<10 sec.; Friability=0%. These values are comparable to that shown in Table 6 for tablets produced with Granule A, wherein the active substance and disintegrant were added extragranularly.

Example 9

Determination of the Active Substance Uptake Capacity for the Direct Tabletting Formulations The active substance uptake capacity goading capacity) of Granule A was compared to that of Ludipress®. Acetaminophen was again used as the sample active substance at increasing levels. The tabletting mixture was produced as described in Example 8 (i.e., 3.5% extragranular crospovidone as disintegrant+acetaminophen in a percentage as indicated in Table 7+Ludipress® or Granule A for the remaining balance). The tabletting results are listed in Table 7. It can be seen that Granule A exhibited excellent uptake capacity.

TABLE 7

|  | Tensile Strength [MPa] (mean ± SD; n = 10) | Disintegration time [sec] | Friability [%] |
|---|---|---|---|
| Ludipress ® |  |  |  |
| No active substance | 0.302 ± 0.043 | <50 | 2.99 |
| 10% Acetaminophen | 0.318 ± 0.070 | <55 | 4.06 |
| 20% Acetaminophen | 0.251 ± 0.066 | <60 | 4.52 |
| 30% Acetaminophen | 0.226 ± 0.055 | <45 | 3.88 |
| 40% Acetaminophen | 0.198 ± 0.035 | <45 | 8.39 |
| Granules A |  |  |  |
| No active substance | 3.355 ± 0.376 | <60 | 0 |
| 10% Acetaminophen | 2.736 ± 0.343 | <45 | 0.40 |
| 20% Acetaminophen | 2.010 ± 0.319 | <30 | 0.40 |
| 30% Acetaminophen | 1.379 ± 0.108 | <20 | 1.41 |
| 40% Acetaminophen | 0.909 ± 0.098 | <20 | 1.84 |
| 50% Acetaminophen | 0.529 ± 0.046 | <40 | 2.67 |

Example 10

The use of Alternative Disintegrants in Conjunction with Direct Tabletting Formulations Other commonly utilized tabletting disintegrants, such as sodium starch glycolate (SSG), reticulated carboxymethylcellulose (croscarmellose, crosslinked CMC) and low-substituted hydroxypropylcellulose (L¢HPC) could be substituted for crospovidone in Examples 5 to 9 to produce tablets with results comparable to that of crospovidone. The optimal concentration range of SSG is from about 4 to about 8% by weight of the total mixture, while croscarmellose and LHPC should be used at a level from about 3 to about 6%. The disintegrant may be added entirely intragranularly (before granulation), entirely extragranularly (after granulation), or split between intragranular and the running powder. The advantage of the third approach is that the extragranule disintegrant first acts to break up the tablet into granules, thereby increasing the surface area available for the intragranular disintegrants to break up the granules.

Comparative Example

Comparison of Tabletting Properties of TAG Granules to that of a Physical Mixture of Microcrystalline Cellulose Grade 101, PVP K30 and 3.5% Crospovidone In this comparison, 3.5% crospovidone was added to Granule A (formed by TAG as described in Example 1) extragranularly such that the combination was compositionally identical to the physical mixture. Additional crospovidone was not added to Granule A' and Ludipress® since these tabletting aids already contain the disintegrant. The results of the comparisons are listed in Table 8. The physical mixture of MCC/PVP K30/crospovidone was not suitable for tabletting because the flow properties were extremely poor (angle of repose=54.67 deg.; BD=0.293 g/ml; TD=0.427 g/ml; Carr's Index=31.27%), especially when compared to that of Granule A (angle of repose=42.67 deg.; BD=0.205 g/ml; TD=0.255 g/ml; Carr's Index=19.69%) which had superior flowability as a result of TAG. The standard deviation for the tensile strength of tablets made with the physical mixture was also larger, as compared to that of those made from TAG granules. Further, despite the addition of crospovidone to aid disintegration, the disintegration time of the resulting tablets from the physical mixture containing acetaminophen was much greater than 15 minutes By comparison, the extragranular addition of crospovidone to granule A resulted in considerably faster disintegration. The slightly longer disintegration time associated with Granule A' compared with Granule A is typical of the phenomenon commonly observed in formulation wherein the use of intragranular disintegrant results in longer disintegration time compared with extragranular disintegrant, due to the ability of extragranular disintegrants to break up the tablet first into the individual granules These comparisons serve to prove that the improvements in overall tabletting properties of granule A over that of MCC 101, or in other granules over the starting diluent excipient, is not due simply to the addition of PVP as a binder The thermal adhesion granulation process described by the present invention is a necessary process to improve the flow properties of the diluent excipients without compromising tablet strength, resistance to fracture, and ease of disintegration

TABLE 8

|  | Tensile Strength [MPa] (mean ± SD; n = 10) | Disintegration time [sec] | Friability [%] |
|---|---|---|---|
| Physical mixture without active substance | 3.754 ± 0.588 | <150 | 0.20 |
| Physical mixture + 30% acetaminophen | 1.495 ± 0.195 | >900 | 0.81 |
| Granules A without active substance | 3.355 ± 0.376 | <60 | 0 |
| Granules A + 30% acetaminophen | 1.379 ± 0.108 | <20 | 1.41 |
| Granule A' without active substance | 3.787 ± 0.192 | <180 | 0.20 |
| Granule A' + 30% acetaminophen | 1.548 ± 0.123 | <40 | 0.40 |
| Ludipress ® without active substance | 0.302 ± 0.043 | <50 | 2.99 |
| Ludipress ® + 30% acetaminophen | 0.226 ± 0.055 | <35 | 3.88 |

Conclusions, Ramifications and Scope

From the above examples and discussions, those skilled in the art can appreciate that the present invention is a simple yet effective and novel means to prepare direct tabletting formulations and aids. Thermal adhesion granulation can be applied to a wide range of diluents, binders and active ingredients, and can utilize both aqueous and organic granulation fluids. The process is an attractive alternative to wet granulation and offers the following advantages:

Due to the significantly lower amount of water utilized, TAG does not decrease the compressibility of MCC, a problem often encountered in wet granulation.

The low amount of granulating fluids utilized, and the potential for granulation in a controlled oxygen-free headspace environment (due to granulation in a closed system), translate to greater drug stability.

The time consuming steps of wet sieving, followed by drying and milling of the granules, are eliminated in TAG.

The low amount of granulating fluids utilized simplifies the manufacturing process and reduces production time. This translates into greater production volume and reduced production costs.

Occupational safety and environmental protection are increased, due to the low solvent requirement of TAG and its ability to accomplish granulate in a confined dosed system.

While the above descriptions and examples contain many specificities, these should not be construed as limitations on the scope of the invention, but rather as an exemplification of one preferred embodiment thereof. Many other variations of TAG are possible. For example, the diluents may be mixed at different ratios, either before or after thermal adhesion granulation, to form tabletting aids with a combination of properties. One such combination is a blend of MCC and lactose to form a tabletting aid with water-insoluble and -soluble portions Yet another possibility is the addition of other tabletting excipients, such as color, flavoring, and glidants (e.g., silicon dioxide or calcium silicate), before or after thermal adhesion granulation. As well, the thermal adhesion granulation process could be applied to suit the particular granulation needs of a variety of industries other than the pharmaceutical industry.

We claim:

1. A thermal adhesion granulation process for preparing direct tabletting formations or aids, comprising the step of subjecting all or part of a mixture comprising:
   (a) from about 5 to about 99% by weight of one or more diluent excipients and/or from 0 to about 99% by weight of a pharmaceutically-active ingredient;
   (b) from about 1 to about 95% by weight of a binder excipient; and optionally with,
   (c) from 0 to about 10% by weight of a disintegrant excipient;
   to heating at a temperature range of from about 30 to about 130° C. under the condition of from about 0.1 to about 20% initial moisture content or from about 0.1 to about 20% initial content of a pharmaceutically-acceptable organic solvent in a closed system with mixing until granules form.

2. A process as defined in claim 1, wherein the temperature range is from about 40 to about 110° C.

3. A process as defined in claim 1, wherein the temperature range is from about 60 to about 105° C.

4. A process as defined in claim 1, wherein the initial moisture content is from about 2 to about 15%.

5. A process as defined in claim 1, wherein the initial moisture content is from about 4 to about 10%.

6. A process as defined in claim 1, wherein the initial organic solvent content is from about 0.1 to about 10%.

7. A process as defined in claim 1, where the initial organic solvent content is from about 0.5 to about 5%.

8. A process as defined in claim 1, wherein the diluent excipient is powdered cellulose, microcrystalline cellulose, lactose, starch, or dibasic calcium phosphate.

9. A process as defined in claim 1, wherein the pharmaceutically-active ingredient is acetaminophen or ascorbic acid.

10. A process as defined in claim 1, wherein the binder excipient is soluble polyvinyl pyrrolidone or hydroxypropylcellulose.

11. A process as defined in claim 1, wherein the disintegrant excipient is crospovidone, sodium starch glycolate, reticulated carboxymethylcellulose, or low-substituted hydroxypropyl cellulose.

12. A process as defined in claim 1, wherein the diluent excipient is microcrystalline cellulose.

13. A process as defined in claim 12, wherein about 90% of the microcrystalline cellulose particles are in the particle size range from about 1 µm to about 125 µm, and the average particle size of the microcrystalline cellulose particles is from about 10 µm to about 70 µm.

14. A process as defined in claim 1, wherein the binder excipient is soluble polyvinyl pyrrolidone.

15. A process as defined in claim 14, wherein the soluble polyvinyl pyrrolidone has a K value of from about 12 to about 120.

16. A process as defined in claim 14, wherein the soluble polyvinyl pyrrolidone has a K value from about 20 to about 95.

17. A process as defined in claim 14, wherein the soluble polyvinyl pyrrolidone has a K value of from about 25 to about 35.

18. A process as defined in claim 1, wherein the binder excipient further contains from 0 to about 10% by weight with respect to the binder of an anticaking agent.

19. A process as defined in claim 18, wherein the binder excipient contains from about 0.01 to about 10% by weight with respect to the binder of an anticaking agent.

20. A process as defined in claim 18, wherein the binder excipient contains from about 2 to about 4% by weight with respect to thee binder of an anticaking agent.

21. A process as defined in claim 18, wherein the anticaking agent is dibasic calcium phosphate anhydrous.

22. A product of the process of claim 1.

23. A tablet which comprises a product as defined in claim 22.

24. A capsule which comprises a product as defined in claim 22.

25. A pellet which comprises a product as defined in claim 22.

26. A thermal adhesion granulation process, which comprises:
   dry-blending binder excipient, one or more diluent excipients, and a pharmaceutically-active ingredient;
   adding water and/or a pharmaceutically-acceptable organic solvent to the dry-blended mixture; and
   heating at a temperature range from about 30° C. to about 130° C. with mixing in a closed system until granules form, wherein:
      the binder excipient is from about 1% to about 95% by weight,
      the one or more diluent excipients are from about 5% to about 99% by weight,
      the pharmaceutically-active ingredient is from 0% to about 99% by weight, and
      the water or the pharmaceutically-acceptable organic solvent is from about 0.1% to about 20% content before heating.

27. The process of claim 26, wherein the mixing is by tumble rotation.

28. A process as defined in claim 26, wherein the temperature range is from about 40 to about 110° C.

29. A process as defined in claim 26, wherein the temperature range is from about 60 to about 105° C.

30. A process as defined in claim 26, wherein the initial content is from about 2 to about 15%.

31. A process as defined in claim 26, wherein the initial content is from about 4 to about 10%.

32. A process as defined in claim 26, wherein the initial organic solvent content is from about 0.1 to about 10%.

33. A process as defined in claim 26, where the initial organic solvent content is from about 0.5 to about 5%.

34. A process as defined in claim 26, wherein the diluent excipient is powdered cellulose, microcrystalline cellulose, lactose, starch, or dibasic calcium phosphate.

35. A process as defined in claim 26, wherein the pharmaceutically-active ingredient is acetaminophen or ascorbic acid.

36. A process as defined in claim 26, wherein the binder excipient is soluble polyvinyl pyrrolidone or hydroxypropylcellulose.

37. The process of claim 26, wherein a disintegrant excipient is included in the dry-blending step.

38. A process as defined in claim 37, wherein the disintegrant excipient is crospovidone, sodium starch glycolate, reticulated carboxymethylcellulose, or low-substituted hydroxypropylcellulose.

39. A process as defined in claim 26, wherein the diluent excipient is microcrystalline cellulose.

40. A process as defined in claim 39, wherein about 90% of the microcrystalline cellulose particles are in the range from about 1 $\mu$m to about 125 $\mu$m, and the average particle size of the microcrystalline cellulose particles is from about 10 $\mu$m to about 70 $\mu$m.

41. A process as defined in claim 26, wherein the binder excipient is soluble polyvinyl pyrrolidone.

42. A process as defined in claim 41, wherein the soluble polyvinyl pyrrolidone has a K value of from about 12 to about 120.

43. A process as defined in claim 41, wherein the soluble polyvinyl pyrrolidone has a K value of from about 20 to about 95.

44. A process as defined in claim 41, wherein the soluble polyvinyl pyrrolidone has a K value of from about 25 to about 35.

45. A process as defined in claim 26, wherein the binder excipient further contains from 0 to about 10% by weight with respect to the binder of an anticaking agent.

46. A process as defined in claim 45, wherein the binder excipient contains from about 0.01 to about 10% by weight with respect to the binder of an anticaking agent.

47. A process as defined in claim 45, wherein the binder excipient contains from about 2 to about 4% by weight with respect to the binder of an anticaking agent.

48. A product prepared by the process of claim 26.

49. A tablet comprising the product of claim 48.

50. A capsule comprising the product of claim 48.

51. A pellet comprising the product of claim 48.

52. The process of claim 1, wherein the mixing is by tumble rotation.

53. A method of making a finely divided powder mixture comprising polyvinyl pyrrolidone, which comprises mixing with the composition dibasic calcium phosphate anhydrous as an anticaking agent in an amount of about 0.01% to about 10% by weight with respect to the polyvinyl pyrrolidone.

54. A finely divided powder mixture prepared by the method of claim 53.

* * * * *